United States Patent [19]
Rockwood, Jr. et al.

[11] Patent Number: 5,314,479
[45] Date of Patent: * May 24, 1994

[54] MODULAR PROSTHESIS

[75] Inventors: Charles A. Rockwood, Jr., San Antonio, Tex.; John A. Engelhardt; Jeffrey M. Ondrla, both of Warsaw, Ind.

[73] Assignee: DePuy Inc., Warsaw, Ind.

[*] Notice: The portion of the term of this patent subsequent to Jan. 14, 2009 has been disclaimed.

[21] Appl. No.: 793,860

[22] Filed: Nov. 18, 1991

Related U.S. Application Data

[63] Continuation-in-part of Ser. No. 529,197, May 25, 1990, Pat. No. 5,080,685, which is a continuation of Ser. No. 450,058, Dec. 13, 1989, Pat. No. 5,181,928, which is a continuation of Ser. No. 896,957, Aug. 15, 1986, abandoned.

[51] Int. Cl.$^5$ ................................................ A61F 2/40
[52] U.S. Cl. ........................................ 623/19; 623/22; 623/18
[58] Field of Search ................ 623/16, 18, 19, 22–23

[56] References Cited

U.S. PATENT DOCUMENTS

| | | |
|---|---|---|
| 2,682,265 | 8/1954 | Collison . |
| 2,719,522 | 10/1955 | Hudack . |
| 2,765,787 | 10/1956 | Pellet . |
| 2,781,758 | 2/1957 | Chevalier . |
| 2,785,673 | 3/1957 | Anderson . |
| 3,064,645 | 11/1962 | Ficat et al. . |
| 3,067,740 | 12/1962 | Haboush . |
| 3,102,536 | 9/1963 | Rose et al. . |
| 3,806,957 | 4/1974 | Shersher . |
| 3,818,512 | 6/1974 | Shersher . |
| 3,863,273 | 2/1975 | Averill . |
| 3,918,441 | 11/1975 | Getscher . |
| 3,987,499 | 10/1976 | Scharbach et al. . |
| 4,051,559 | 10/1977 | Pifferi . |
| 4,115,875 | 9/1978 | Rambert et al. . |
| 4,404,691 | 9/1983 | Buning et al. . |
| 4,459,708 | 7/1984 | Buttazzoni . |
| 4,488,319 | 12/1984 | von Recüm . |
| 4,532,660 | 8/1985 | Field . |
| 4,578,081 | 3/1986 | Harder et al. . |
| 4,655,778 | 4/1987 | Koeneman .............. 623/18 |
| 4,676,797 | 6/1987 | Anapliotis et al. . |
| 4,698,063 | 10/1987 | Link et al. . |
| 4,822,370 | 4/1989 | Schelhas ................. 623/18 |
| 4,840,632 | 6/1989 | Kampner . |
| 4,842,606 | 6/1989 | Kranz et al. ............ 623/18 |
| 4,865,605 | 9/1989 | Dines et al. . |
| 4,963,155 | 10/1990 | Lazzeri et al. .......... 623/23 |
| 5,002,581 | 3/1991 | Paxson et al. .......... 623/18 |
| 5,032,130 | 7/1991 | Schelhas et al. ....... 623/23 |
| 5,080,685 | 1/1992 | Bolesky et al. ........ 623/18 |

FOREIGN PATENT DOCUMENTS

| | | |
|---|---|---|
| 0163121A1 | 4/1985 | European Pat. Off. . |
| 0198163A2 | 2/1986 | European Pat. Off. . |
| 0190981A1 | 8/1986 | European Pat. Off. . |
| 1183230 | 12/1973 | France . |
| 2225141 | 8/1974 | France . |
| 2378505 | 7/1976 | France . |
| 2575-383A | 12/1984 | France . |
| 2576793 | 1/1985 | France . |
| 1531487 | 11/1974 | United Kingdom . |
| 1443470 | 7/1976 | United Kingdom . |
| 1521679 | 8/1978 | United Kingdom . |
| 2070939 | 9/1981 | United Kingdom . |
| WO83/02555 | 8/1983 | World Int. Prop. O. . |

OTHER PUBLICATIONS

Tumorprotheses des Hüftgelenkes (Indikation und Ergebnisse); by: M. Jäger, L. Löffler, D. Kohn.

Concept and Material Properties of Cementless Hip Prosthesis System with $Al_2O_3$ Ceramic Ball Heads and Wrought Ti-6A1-4V Stems; By: K. Zweymüller and M. Semlitsch.

Primary Examiner—David Isabella
Assistant Examiner—Gina M. Gualtieri
Attorney, Agent, or Firm—Barnes & Thornburg

[57] ABSTRACT

A modular shoulder prosthesis for the replacement of a portion of the humerus is provided. The prosthesis is assembled from a kit that includes a stem sized to be received in the humerus, a body sized to replace a portion of the humerus, the body being attachable to the stem, and a head member sized to replace the head of the humerus, the head member being eccentrically attachable to the body. A collar is inserted between the head member and the body to help stabilize the assembled prosthesis.

45 Claims, 3 Drawing Sheets

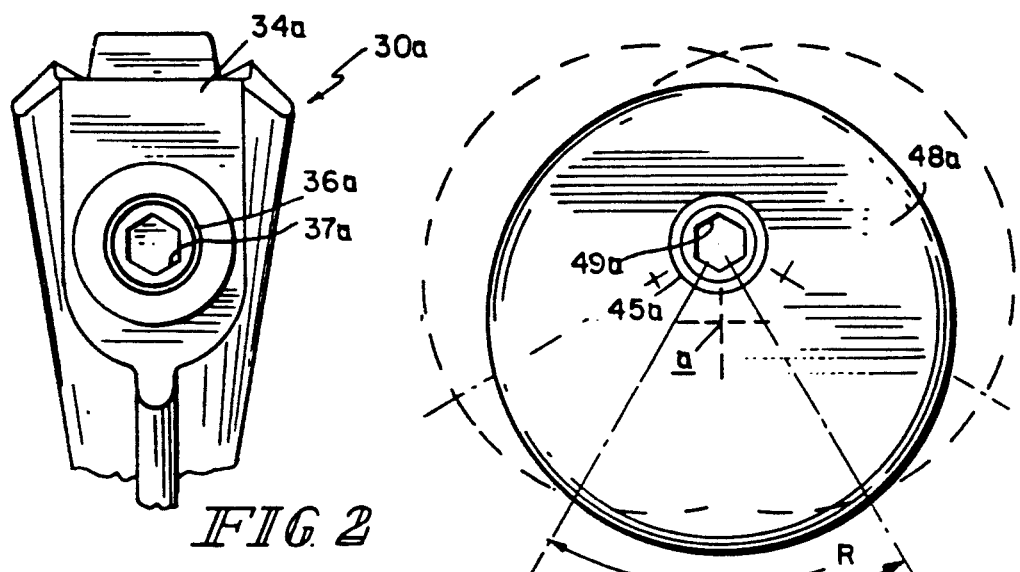
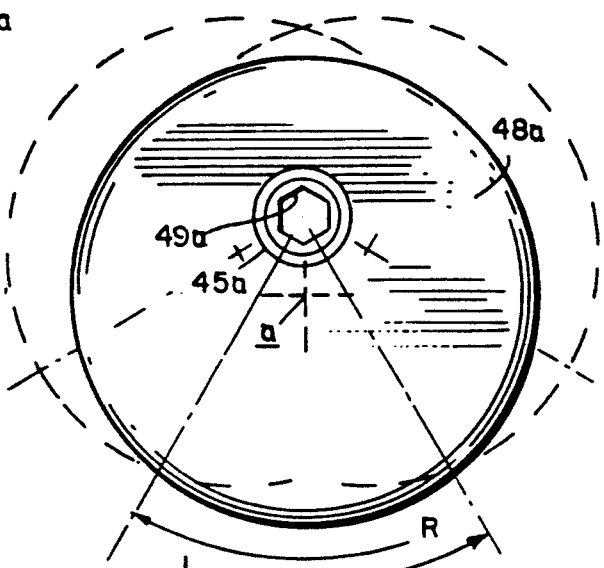
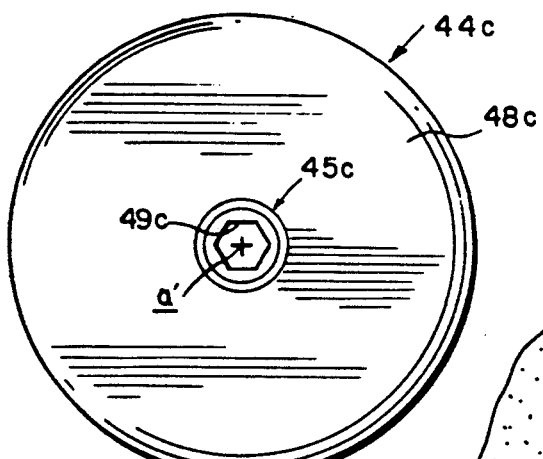
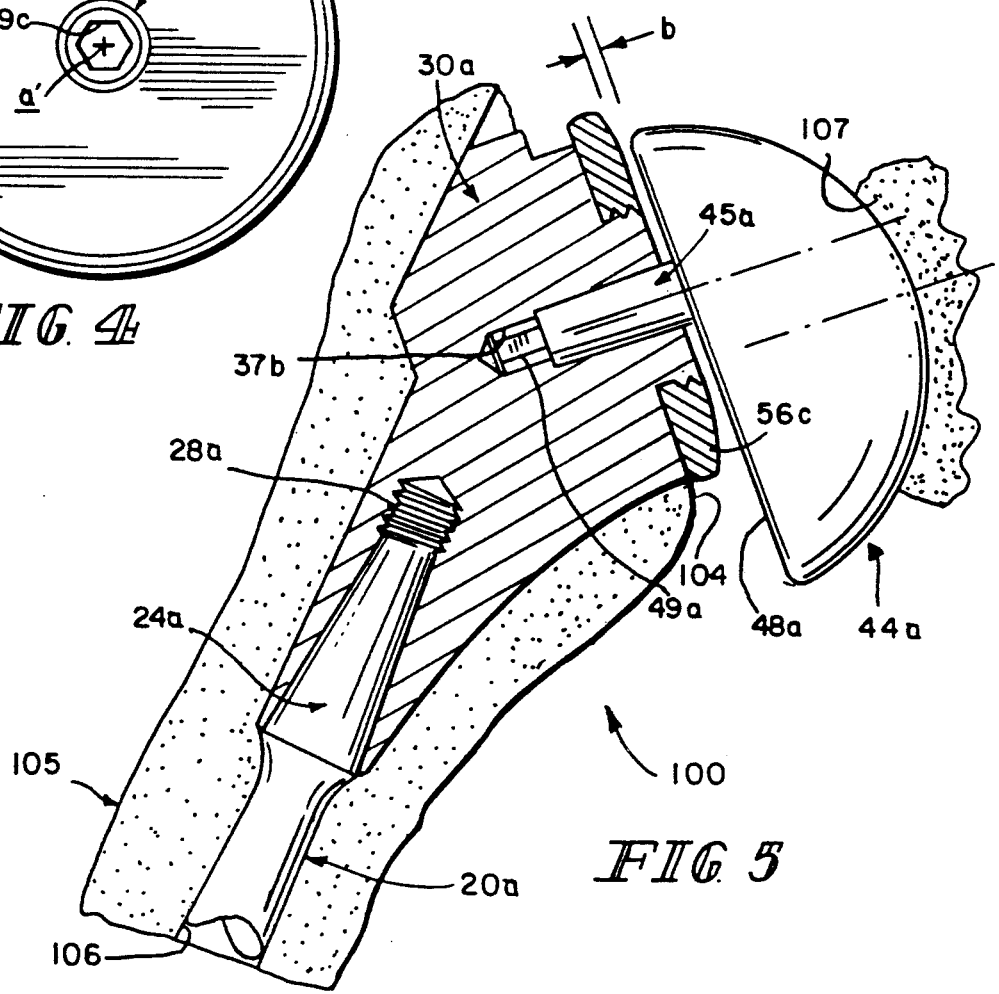
FIG. 2
FIG. 3
FIG. 4
FIG. 5

MODULAR PROSTHESIS

This application is a continuation-in-part of application Ser. No. 529,197, filed May 25, 1990, now U.S. Pat. No. 5,080,685, issued Jan. 14, 1992, which is a continuation of Ser. No. 450,058, filed Dec. 13, 1989, now U.S. Pat. No. 5,181,928, which is a continuation of Ser. No. 896,957, filed Aug. 15, 1986, now abandoned.

BACKGROUND AND SUMMARY OF THE INVENTION

The present invention relates to prostheses for replacement of a portion of the shoulder joint. More particularly, the present invention relates to a modular prosthesis for replacement of the upper portion of the humerus.

Conventional prostheses for the replacement of the upper portion of the humerus are typically unitary structures, generally including a stem designed to extend downwardly into a cavity within the humerus. The stem of the conventional prostheses is secured within the bone of the humerus by bone cement or through the use of coatings that promote bone ingrowth to secure the stem. The stem is attached to a body portion designed to replace portions of the humerus in the vicinity of the anatomical neck of the humerus. The conventional shoulder prosthesis also includes a generally spherical head portion configured to replace the head of the humerus. A collar is generally provided between the head portion and the stem to stabilize the prosthesis on the resected humerus. Generally, the collar rests on the resected surface of the humerus to distribute imposed loading on the prosthesis over a greater area of bone.

One difficulty with conventional unitary shoulder prostheses is the necessity of maintaining large inventories of differently sized prostheses to accommodate the different bone sizes of prospective patients. With such unitary shoulder prostheses, the patient is typically evaluated by x-ray to determine the approximate prosthesis size needed for bone replacement. A number of differently sized prostheses are selected as possible candidates for bone replacement on the basis of this evaluation, and the final selection of the appropriate prosthesis is selected during the replacement operation.

Fully or partially modular prostheses that diminish the problem of maintaining a large inventory are known for use as femur replacements. For example, U.S. Pat. No. 4,051,559 discloses a prosthesis that includes a separate threaded stem that is adapted to be screwed into a prepared cavity within the femur. The prosthesis separately comprises a head portion that includes a neck and collar that is adapted to be mated with the stem. This prosthesis is not designed to be assembled prior to insertion within the patient. The stem must first be screwed into the cavity within the femur. The head portion is then attached to the installed stem by a bolt. The collar is designed to rest upon the resected surface of the femur to support the load placed on the prosthesis. Because of the design of the stem, the head portion must include the collar in order to support the weight that will be placed on the prosthesis. The modularity of this prosthesis is limited because the neck and collar is a unitary structure.

Another prosthesis having a stem and a separate head portion is shown in U.S. Pat. No. 3,806,957, which discloses a prosthesis that includes a separate stem having a broadened proximal end. The broadened proximal end of the stem is configured to receive a head and threaded neck portion to form a complete prosthesis. The neck may be elongated or shortened depending on the specific anatomy of different patients. This prosthesis, like the prosthesis disclosed in U.S. Pat. No. 4,051,559, is limited in flexibility because the head and neck portion is a unitary structure, and because the head and neck portion attaches directly into the stem.

A prosthesis in which the stem comprises more than one component is shown in U.S. Pat. No. 3,987,499. U.S. Pat. No. 3,987,499 discloses a prosthesis having a stem or shank component that includes two parts, an anchoring part and a transition part. A ball is connected to the transition part. Also, a collar may be included between the ball and a portion of the femur. The anchoring part is provided with external threads that are adapted to tap themselves into the femur. The transition part is coupled to the anchoring part by a guide pin and securing screw. The ball is adapted to be screwed onto the free end of the transition part. The prosthesis is designed to be placed in position within the body component by component, and assembled sequentially.

In addition to modular femoral prostheses, partially modular humeral prostheses have been described. For example, U.S. Pat. No. 4,865,605 to Dines et al. discloses a shoulder prosthesis having a humeral component and a glenoid component. The humeral component includes a stem and an integrally attached collar. A spherical head having a stem fittable into a tapered bore in the stem of the humeral component to provide a friction tight attachment between the head and the stem of the humeral component is also described. Both the head and the stem of the humeral component are available in different sizes.

According to the present invention, a kit for the assembly of a shoulder prosthesis for the replacement of a portion of a humerus is provided. The kit includes at least two stems of differing size, with each stem sized for insertion into the humerus and at least two bodies, with each body sized to replace a portion of the humerus. In addition, the kit includes at least two head members, with each head member sized to replace the head of the humerus. Attachment means for fixedly attaching one of the at least two head members to one of the at least two bodies is also provided. Optionally, the kit can contain at least two collars, with each collar configured to be positioned between one of the at least two head members and one of the at least two bodies to contact humeral bone and stabilize the position of the inserted shoulder prosthesis.

Preferably, the kit of the present invention consists of a plurality of stems, bodies, collars, and head members all having various sizes and shapes. These separate components are adapted to be assembled together to form a custom prosthesis of a desired size and shape. One advantage of this feature is that a shoulder prosthesis of a desired size and shape may be assembled from the kit at the time of the operation. Another advantage results from the large number of varying configuration shoulder prostheses that can be assembled from the component parts without needing to increase the number of assembled shoulder prostheses maintained in hospital inventory.

Another preferred embodiment of the present invention provides for an implant apparatus for replacing a portion of a humerus that includes a body formed to define a bore therein. A head member sized to replace the head of the humerus is eccentrically or centrally attached to the body. Eccentric attachment allows adjustable superior/inferior or anterior/posterior positioning of the head member relative to the body to provide a better fit for the implanted shoulder prosthesis. In preferred embodiments, the eccentric or central attachment is maintained by the interaction of a locking socket defined in the bore of the body to have a polygonal cross section, and a lock finger defined by the head member to present a lock element configured to fit in the locking socket. The locking socket can be formed to have a hexagonal cross section and the lock element of the lock finger hexagonally configured to fit in the locking socket so that the head member can be positioned relative to the body in one of six possible orientations.

The modular shoulder prosthesis of the present invention thus provides the ability to assemble a custom prosthesis by selecting different sizes, shapes, and orientations of individual components to meet the requirements of the individual patient exactly. The provision of the kit greatly reduces the inventory required to be maintained by the hospital. Also, the kit form of the prosthesis increases greatly the flexibility of the implant apparatus, and provides for the assembly of a prosthesis that may otherwise be unavailable.

Additional objects, features, and advantages of the invention will be apparent to those skilled in the art upon consideration of the following detailed description of preferred embodiments exemplifying the best mode of carrying out the invention as presently perceived.

BRIEF DESCRIPTION OF THE DRAWINGS

The detailed description particularly refers to the accompanying figures in which:

FIG. 2 is a top plan view of the body, illustrating the bore configured to engage and lock the hexagonal lock finger of the head member;

FIG. 3 illustrates asymmetric attachment of a hexagonal lock finger on a head member; and FIG. 4 illustrates central Positioning of a hexagonal lock finger on the head member:

FIG. 5 is a cross sectional view of one possible combination of stem, body, collar, and head member selected from the kit of FIG. 1 and assembled and installed in a humerus.

DETAILED DESCRIPTION OF THE DRAWING

Figure 1:
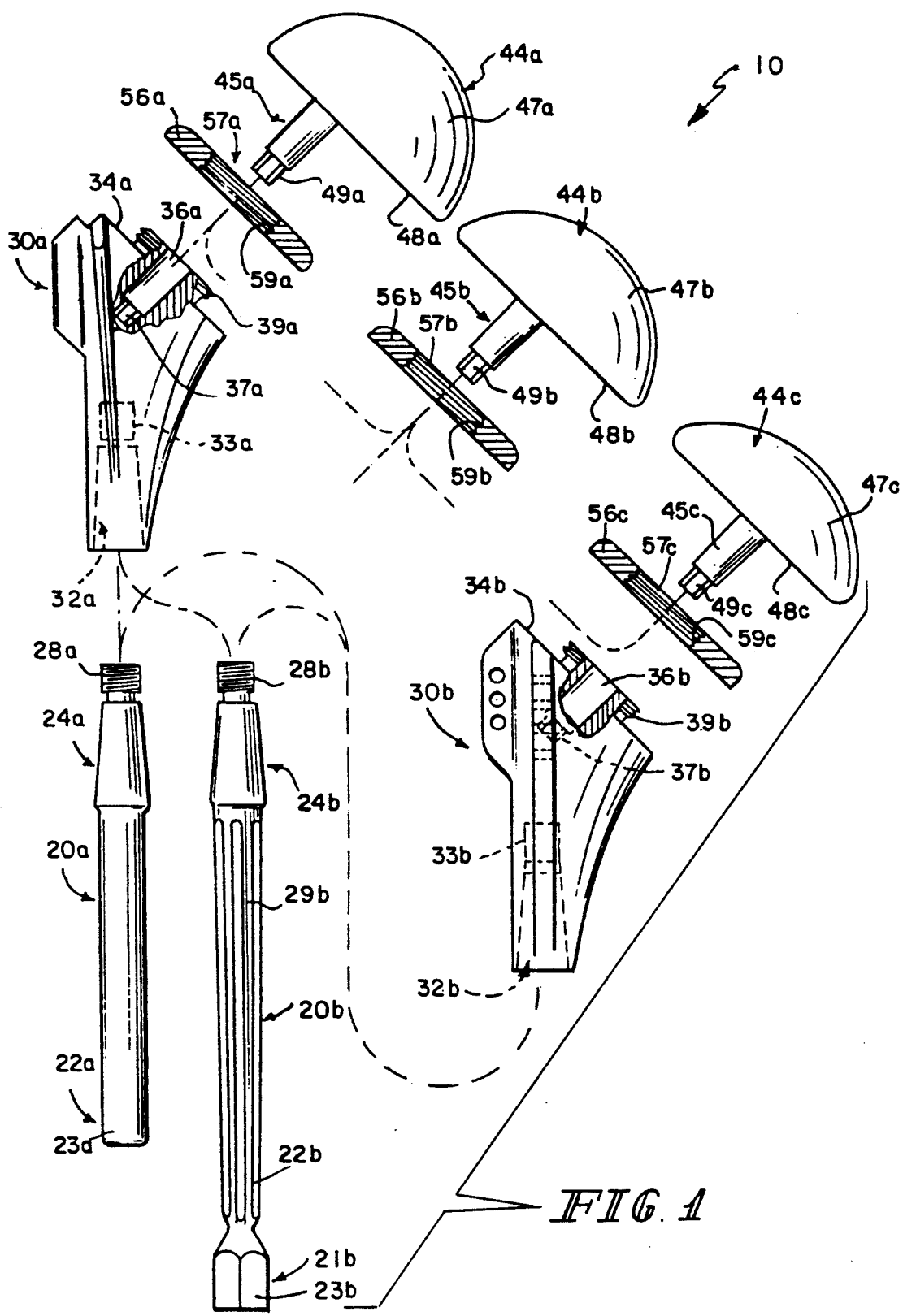
FIG. 1 is an exploded perspective view of a modular humeral prostheses kit showing two differently sized and shaped stems, two differently sized and shaped bodies attachable to the stems, three differently sized head members attachable to the bodies, and three differently sized collars that can be positioned between the head and the body.

As shown in FIG. 1, a kit 10 for assembly of a humeral prosthesis has multiple differently sized and shaped components, including stems 20a and 20b, bodies 30a and 30b, collars 56a, 56b, and 56c, and head members 44a, 44b, and 44c. An implant apparatus for replacement of the head, neck, and adjacent portions of a humerus can be assembled by conjoining one stem selected from the group of stems 20a and 20b, one body selected from the group of bodies 30a and 30b, and one head member selected from the group of head members 44a, 44b, and 44c. Optionally, a collar can be selected from the group of collars 56a, 56b, and 56c for positioning between the selected head member and the selected body. Provision of the kit 10 allows assembly of a humeral prosthesis having a desired size and shape without requiring a large inventory of differently sized and shaped unitary prostheses for replacement of portions of the humerus.

Two differently sized and shaped stems 20a and 20b are illustrated in FIG. 1. Stem 20a has a generally cylindrical shape, and is configured to have a lower portion 22a and an upper portion 24a. The upper portion 24a terminates with exterior threads 28a configured for screwing attachment to either body 30a or 30b. The lower portion 22a of the stem 20a is designed to be inserted into a cavity in a humerus (not shown).

The stem 20b also has a generally cylindrical shape, but it is sized to have a greater length and radius than that of stem 20a to accommodate attachment to larger humeri. The stem 20b has an upper portion 24b terminating in external threads 28b that allow screwing attachment of the stem 20b to either body 30a or 30b. The stem 20b is configured to have a plurality of channels 29b cut into its lower portion 22b to provide bone ingrowth sites. Of course, bone cements known in the art can be used to promote both short and long term fixation of the stem 20b to a humerus.

The lower portion 22b of the stem 20b terminates in a frangible torque-limiting element 21b that includes a tightening piece 23b and a breakable neck 25b. Provision of the torque limiting element 21b allows an operator to apply just the necessary amount of torque required to tighten the external threads 28b of the stem 20b in permanent attachment to one of the bodies 30a or 30b. In practice, an operator temporarily mounts one of the bodies 30a or 30b in a clamp or vise that prevents rotation of the body 30a or 30b. The stem 20b is Positioned with respect to the clamped body 30a or 30b so that its external threads 28b threadingly engage internal threads 33a or 33b defined in bores 32a or 32b of the respective bodies 30a or 30b. A wrench or other torque application means (not shown) is used by an operator to twist the tightening piece 23b in a clockwise direction, causing threaded engagement of the stem 20b to one of the bodies 30a or 30b. The torque limiting element 21b prevents overtightening of the stem 20b to one of the bodies 30a or 30b because application of excessive torque by an operator to the tightening piece 23b causes the tightening piece 23b to snap-off from the lower portion 22b of the stem 20a at the site of the breakable neck 25b. Appropriate selection of the thickness of the breakable neck 25b allows one to set a predetermined limit to the amount of torque that can be applied to the stem 20b for threaded engagement of stem 20b with one of body 30a or body 30b.

Bodies 30a and 30b also include surfaces 34a, 34b into which bores 36a and 36b respectively have been defined. The bores 36a and 36b are configured so that at least a portion of the bores 36a, 36b have a non-circular cross section. Preferred non-circular cross sections include ellipses, polygonal cross sections including regular symmetric convex polygons such as squares, hexagons, and dodecagons, regular symmetric concave polygons including 6, and 8 pointed stars, and asymmetric convex or concave polygons, such as rhombuses or trapezoids. As best seen in FIG. 2, a locking socket 37a of the bore 36a is formed to have a regular, symmetric hexagonal cross section. Body 30b is formed to have a similarly dimensioned hexagonal locking socket 37b (shown in outline in FIG. 1). The bodies 30a and 30b may be formed by casting, machining, or forging and can optionally have any of the bone growth or cement enhancement promoting surface coatings or treatments such as grist blast, etc.

Head members 44a, 44b, and 44c are sized to replace the head of the humerus and are accordingly configured as partial spheroids. Spherical portions 47a, 47b, or 47c of the head members 44a, 44b, or 44c, when implanted, ride in the glenoid cavity or articulate with the acromion of the shoulder When an implantable humeral prosthesis is assembled (for example, such as illustrated in FIG. 5) the truncated portions 48a, 48b, and 48c respectively of the head members 44a, 44b, and 44c are positioned to oppose one of the bodies 30a or 30b. The head members 44a, 44b, and 44c are receivably held in fixed attachment to one of the bodies 30a or 30b by a lock finger 45a, 45b, or 45c that slightly tapers to form a friction tight taper lock (ie. Morse lock) with one of the bores 36a or 36b of the bodies 30a, 30b. The lock fingers 45a, 45b, or 45c are eccentrically (for example, as with head members 44a and 44b) or centrally (as for example with head member 44c) mounted on the truncated portion 48a, 48b, or 48c of the head members 44a, 44b, or 44c. Eccentric mounting of head members 44a and 44b involves permanent attachment (or integral formation) of the lock finger 45a to the truncated portion 48a or 48b in a non-central position (the center of the truncated portion 44a is indicated by point a in FIG. 3) to advantageously permit the head member 44a to be rotated relative to the bodies 30a or 30b for movement anteriorly, posteriorly, inferiorly, or superiorly as required for best fit. Three of six possible positions relative to body 30a or body 30b into which head member 47a can be permanently attached are shown in FIG. 3. A lock finger 45c centrally attached to the truncated portion 48c of the head member 44c (best seen in FIG. 4, center point of truncated portion 48c indicated by a') can optionally be used when central positioning of the lock finger is desirable.

Locking attachment to prevent rotational movement of head members 44a, 44b, or 44c with respect to body 30a or body 30b relies on interaction between the locking sockets 37a, 37b defined in the bodies 30a or 30b and lock elements 49a, 49b, or 49c distally defined by the lock fingers 45a, 45b, or 45c. The lock elements 49a, 49b, and 49c have identical hexagonal cross sections to permit interchangeability, and are sized to snugly fit into the locking sockets 37a or 37b to lock the head members 44a, 44b, or 44c in one of six possible orientations relative to the bodies 30a or 30b. Of course, when a lock finger is centrally attached to a head member, as for example lock finger 45c of head member 44c, all six orientations are indistinguishable from each other because of the radial symmetry of the head member 44c. As can be appreciated, for proper fit into the locking sockets, the lock elements should have an appropriately sized non-circular cross sections equivalent to the cross section of lock element.

Generally, one of collars 56a, 56b, or 56c is positioned between the head members 44a, 44b, or 44c and bodies 30a or 30b. The collars 56a, 56b, and 56c are substantially flat annular disks dimensioned to have a radius smaller than the head member 44a, 44b, 44c with which it is to be used. The collars 56a, 56b, 56c are formed to respectively define an opening 57a, 57b, or 57c. The openings 57a, 57b, or 57c are dimensioned to allow passage therethrough of the lock fingers 45a, 45b, or 45c and are formed so that interior threads 59a, 59b, and 59c are respectively defined. These threads 59a, 59b, and 59c can threadingly engage one of exterior threads 39a or 39b defined respectively in body 30a and 30b to tightly hold collars 56a, 56b, or 56b to one of bodies 30a, 30b. The collars 56a, 56b, or 56c are useful for stabilizing the position of the body 30a or 30b with respect to the humerus, and help distribute compressive forces over a larger area of dense, tough humeral cortical bone.

FIG. 5 illustrates a humeral prosthesis 100 assembled from selected modular components of the kit 10 illustrated in FIG. 1. The humeral prosthesis includes stem 20a imbedded in a humerus 105, with its upper portion 24a threadingly engaged (with external threads 28a) to the body 30b. A collar 56c is attached to the body 30b in its proper position between the body 30b and the head member 44a, leaving a gap b between the collar 56c and head member 44a. The collar may be attached to the body with a preselected amount of torque by any of a variety of assembly tools (not shown) so that the collar is securely attached. The lock element 49a of the lock finger 45a is positioned to engage the locking socket defined in the body 30b so that the head member 44a is inferiorly (downwardly) disposed.

The humeral prosthesis 100 is inserted into a humerus 105 in which the head and neck portions (not shown) have been resected. The resection of the head and neck portions of the humerus 105 has been performed to leave a generally planar surface 104 on the humerus 105. A cavity 106 has been formed in the humerus 105 to receive stem 20a of the prosthesis 100. It will be understood that the resection procedure and the procedure for forming the cavity 106 are well known in the art.

To install the assembled prosthesis 100 in the humerus 105, a bone cement material is generally first injected into the cavity 106. The prosthesis 100 is then placed in the cavity 106 such that the distal end of the body 30b rests upon surface 104 of the resected humerus 105, and stem 20a extends downwardly into the cavity 106. The cement surrounds the stem 20a and in some cases a portion of the body 30b and acts to secure the prosthesis 100 within the humerus 105. The head member 44a is then positioned to fit into a glenoid cavity 107 of the shoulder.

Figure 6:
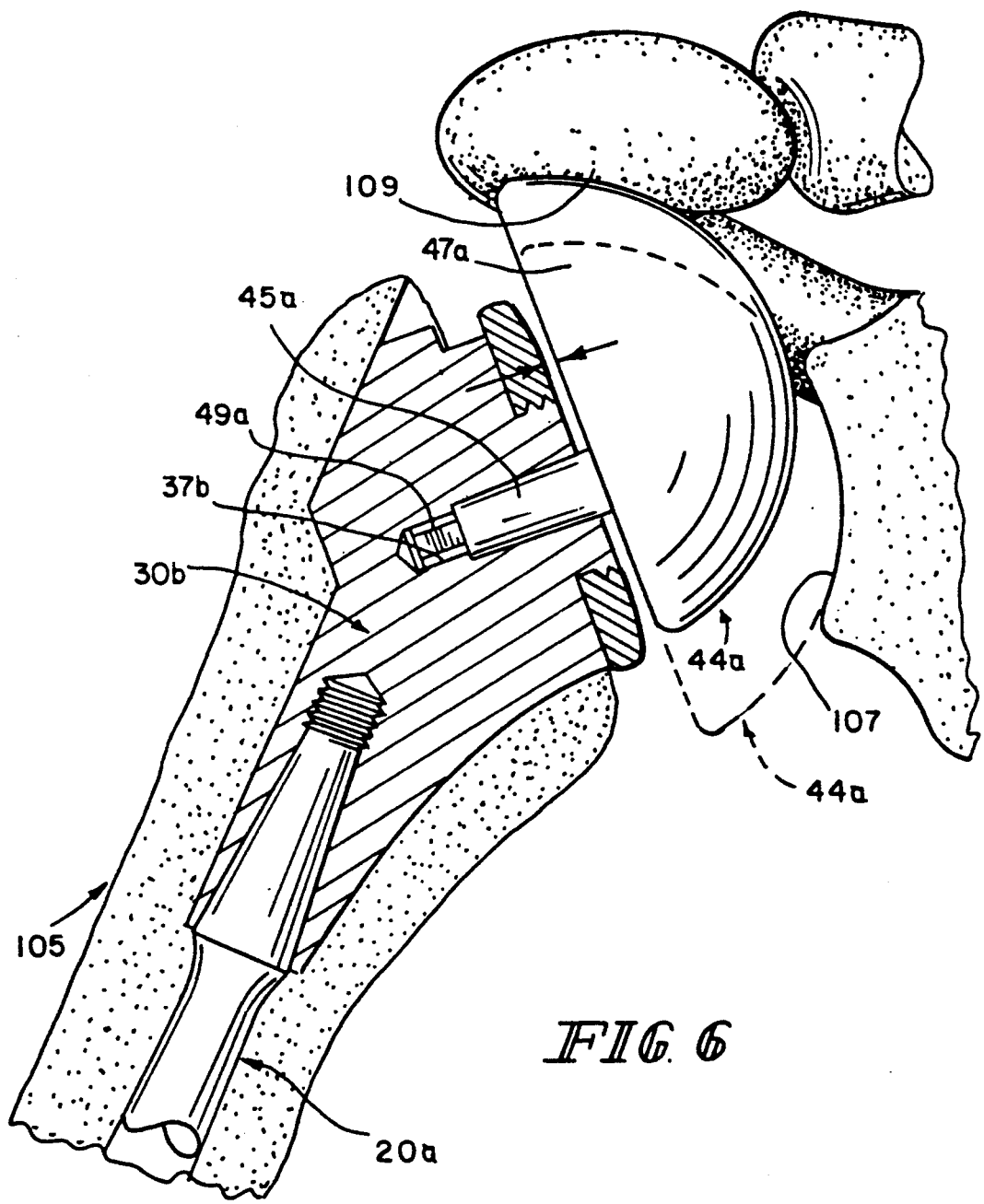
FIG. 6 is an alternative embodiment showing an eccentrically mounted head member articulating with the acromion of a patient.

FIG. 6 illustrates an alternative positioning of eccentrically mounted head member 44a, with the lock element 49a and head member 44a rotated 180 degrees to a superior position. This orientation allows articulation of the partially spheroidal head portion 47a with an acromion 109, for those situations where the glenoid cavity has been damaged or is otherwise unsuitable for accomodating the head member 44a (eg. rotator cuff deficient patients).

It will be understood that the components shown in the figures may be interchangeable with other components of the kit 10, and a humeral prosthesis may be assembled utilizing combinations of the illustrated components selected from the kit 10. This ability to select different sizes and shapes of components to assemble a prosthesis greatly enhances the flexibility available at the time of the operation. Thus, depending upon the anatomical indications presented by the patient, numerous combinations are available to assemble a prosthesis at the time of the operation to meet the exact requirements for that patient.

Although the invention has been described in detail with reference to preferred embodiments and specific examples, variations and modifications exist within the scope and spirit of the invention as described and defined in the following claims.

What is claimed is:

1. A kit for the assembly of a modular shoulder prosthesis for the replacement of a head, neck, and adjacent portions of a humerus, the kit comprising
   at least two stems, with each stem sized for insertion into the humerus,
   at least two bodies, with each body sized to replace a portion of the humerus, and with each body configured to receive in fixed attachment one of the at least two stems,
   at least two head members, with each head member sized to replace the head of the humerus, and
   means for fixedly attaching one of the at least two head members to one of the at least two bodies.

2. The kit of claim 1 further comprising at least two collars, with each collar configured for positioning between one of the at least two bodies and one of the at least two head members so that the collar can increase stability of the assembled modular shoulder prosthesis.

3. The kit of claim 1, wherein at least one of the stems is attached to at least one of the bodies with external threads defined on the at least one stem and internal threads defined in a bore in the at least one body for threaded engagement of the stem and the body.

4. The kit of claim 3, wherein at least one of the stems further comprises frangible means for limiting torque application to the stem, the frangible means configured to break and prevent further tightening of the stem upon application of a predetermined amount of torque acting to tighten the threaded engagement of the stem and the body.

5. The kit of claim 1, wherein means for fixedly attaching one of the at least two head members to one of the at least two bodies further comprises a lock finger attached to one of the at least two head members, the lock finger being formed to define a lock element having a non-circular cross section to prevent rotation of the lock finger relative to the one of at least two bodies.

6. The kit of claim 5, wherein the lock finger attached to one of the at least two head members is centrally attached.

7. The kit of claim 5, wherein the lock finger attached to one of the at least two head members is eccentrically attached.

8. An implant apparatus for replacing a portion of a humerus, the implant comprising
   a body formed to define a first and second bore therein,
   a stem having an upper portion and a lower portion, the lower portion being sized to be received in a shaft of a humerus and the upper portion configured to fit in the first bore of the body, and
   a head member sized to replace a head portion of the humerus, the head member having an attached lock finger configured to fit in the second bore of the body.

9. The implant apparatus of claim 8, wherein the lock finger is eccentrically attached to the head member.

10. The implant apparatus of claim 9, wherein the second bore of the body is formed to define a locking socket having a hexagonal cross section and the lock finger further comprises a hexagonal lock element configured to fit in the locking socket so that the head member can be positioned relative to the body in one of six possible orientations.

11. The implant apparatus of claim 8 further comprising a collar positioned between the head member and the body to stabilize the position of the body relative to a humerus.

12. The implant apparatus of claim 11, wherein the collar is formed to define an central opening sized to permit passage therethrough of the lock finger.

13. The implant apparatus of claim 8, wherein the stem is configured to present a bone ingrowth surface to facilitate long-term attachment of the stem to the humerus.

14. The implant apparatus of claim 13, wherein the first bore is formed to define internal threads and wherein the stem further comprises external threads defined on the upper portion of the stem, the external threads being dimensioned to match the internal threads to permit threaded engagement of the stem and the body.

15. The apparatus of claim 14, wherein the stem further comprises frangible means for limiting torque application to the stem, the frangible means configured to break and prevent further tightening of the stem upon application of a predetermined amount of torque acting to tighten the threaded engagement of the stem and the body.

16. An implant apparatus for replacing a portion of a humerus, the implant comprising
   a body formed to define a bore therein,
   a head member sized to replace a head portion of the humerus,
   means for eccentric attachment of the head member to the body to allow adjustable positioning of the head member relative to the body.

17. The implant apparatus of claim 16, wherein the eccentric attachment means further comprises a lock finger eccentrically attached to the head member.

18. The implant apparatus of claim 17, wherein the bore of the body is formed to define a locking socket having a non-circular cross section and the lock finger further comprises a lock element configured to lockingly fit in the locking socket.

19. The implant apparatus of claim 18, wherein the locking socket has a hexagonal cross section and the lock element of the lock finger further comprises a hexagonal lock element sized to fit in the locking socket so that the head member can be positioned relative to the body in one of six possible orientations.

20. A kit for the assembly of a modular bone joint prosthesis for the replacement of a head, neck, and adjacent portions of a bone, the kit comprising
   at least two stems, with each stem sized for insertion into a cavity of the bone,
   at least two bodies, with each body sized to replace a portion of the bone, and with each body configured to be joined in fixed attachment to one of the at least two stems,
   at least two head members, with each head member sized to replace a head portion of the bone, and
   means for fixedly attaching one of the at least two head members to one of the at least two bodies.

21. The kit of claim 20 further comprising at least two collars, with each collar configured for positioning between one of the at least two bodies and one of the at least two head members so that the collar can increase stability of the assembled modular joint prosthesis.

22. A kit for the assembly of a modular bone joint prosthesis for the replacement of a head, neck, and adjacent portions of a bone, the kit comprising
   at least two stems, with each stem sized for insertion into a cavity of the bone,
   at least two bodies, with each body sized to replace a portion of the bone, and with each body configured to be joined in fixed attachment to one of the at least two stems,
   at least two head members, with each head member sized to replace a head portion of the bone,
   means for fixedly attaching one of the at least two head members to one of the at least two bodies, and
   wherein at least one of the stems is attached to at lead one of the bodies with external threads defined on the at least one stem and internal threads defined in a bore in the at least one body for threaded engagement of the stem and the body.

23. The kit of claim 22, wherein at least one of the stems further comprises frangible means for limiting torque application to the stem, the frangible means configured to break and prevent further tightening of the stem upon application of a predetermined amount of torque acting to tighten the threaded engagement of the stem and the body.

24. The kit for the assembly of a modular bone joint prosthesis for the replacement of a head, neck, and adjacent portions of a bone, the kit comprising
   at least two stems, with each stem sized for insertion into a cavity of the bone,
   at least two bodies, with each body sized to replace a portion of the bone, and with each body configured to be joined in fixed attachment to one of the at least two stems,
   at least two head members, with each head member sized to replace a head portion of the bone,
   means for fixedly attaching one of the at least two head members to one of the at least two bodies, and
   wherein the means for fixedly attaching one of the at least two head members to one of the at least two bodies further comprises a lock finger attached to one of the at least two head members, the lock finger being formed to define a lock element having a non-circular cross section to prevent rotation of the lock finger relative to the one of at least two bodies.

25. The kit of claim 24, wherein the lock finger attached to one of the at least two head members is centrally attached.

26. The kit of claim 24, wherein the lock finger attached to one of the at least two head members is eccentrically attached.

27. The kit of claim 20, wherein one of the at least two stems has a different size and shape as another of the at least two stems.

28. The kit of claim 20, wherein one of the at least two bodies has a different size and shape as another of the at least two bodies.

29. The kit of claim 27, wherein one of the at least two bodies has a different size and shape as another of the at least two bodies.

30. The kit of claim 20, wherein one of the at least two head members has a different size and shape as another of the at least two head members.

31. The kit of claim 27, wherein one of the at least two head members has a different size and shape as another of the at least two head members.

32. The kit of claim 28, wherein one of the at least two head members has a different size and shape as another of the at least two head members.

33. The kit of claim 29, wherein one of the at least two head members has a different size and shape as another of the at least two head members.

34. An implant apparatus for replacing a joint portion of a bone, the implant comprising
   a body formed to define a first and second bore therein,
   a stem having an upper portion and a lower portion, the lower portion being sized to be received in a cavity of the bone and the upper portion configured to fit in the first bore of the body, and
   a head member sized to replace a head portion of the bone, the head member having an attached lock finger configured to fit in the second bore of the body.

35. The implant apparatus of claim 34, wherein the lock finger is eccentrically attached to the head member.

36. The implant apparatus of claim 35, wherein the second bore of the body is formed to define a locking socket having a hexagonal cross section and the lock finger further comprises a hexagonal lock element configured to fit in the locking socket so that the head member can be positioned relative to the body in one of six possible orientations.

37. The implant apparatus of claim 34, further comprising a collar positioned between the head member and the body.

38. The implant apparatus of claim 37, wherein the collar is formed to define an central opening sized to permit passage therethrough of the lock finger.

39. The implant apparatus of claim 34, wherein the stem is configured to present a bond ingrowth surface to facilitate long-term attachment of the stem in the bone cavity.

40. The implant apparatus of claim 39, wherein the first bore is formed to define internal threads and wherein the stem further comprises external threads defined on the upper portion of the stem, the external threads being dimensional to match the internal threads to permit threaded engagement of the stem and the body.

41. The apparatus of claim 40, wherein the stem further comprises frangible means for limiting torque application to the stem, the frangible means configured to break and prevent further tightening of the stem upon application of a predetermined amount of torque acting to tighten the threaded engagement of the stem and the body.

42. An implant apparatus for replacing a joint portion of a bone, the implant comprising
   a body formed to define a bore therein,
   a head member sized to replace a head portion of the bone,
   means for eccentric attachment of the head member to the body to allow adjustable positioning of the head member relative to the body.

43. The implant apparatus of claim 42, wherein the eccentric attachment means further comprises a lock finger eccentrically attached to the head member.

44. The implant apparatus of claim 43, wherein the bore of the body is formed to define a locking socket having a non-circular cross section and the lock finger further comprises a lock element configured to lockingly fit in the locking socket.

45. The implant apparatus of claim 44, wherein the locking socket has a hexagonal cross section and the lock element of the lock finger further comprises a hexagonal lock element sized to fit in the locking socket so that the head member can be positioned relative to the body in one of six possible orientations.

* * * * *

UNITED STATES PATENT AND TRADEMARK OFFICE
CERTIFICATE OF CORRECTION

PATENT NO. : 5,314,479
DATED : May 24, 1994
INVENTOR(S) : Charles A. Rockwood, Jr.

It is certified that error appears in the above-indentified patent and that said Letters Patent is hereby corrected as shown below:

Claims 20, 21 and 27-33 should be deleted;
Col 9 line 15 (claim 22) "lead" should be "least"

Signed and Sealed this

Thirteenth Day of December, 1994

Attest:

BRUCE LEHMAN

Attesting Officer

Commissioner of Patents and Trademarks